(12) United States Patent
Muray et al.

(10) Patent No.: US 7,332,729 B1
(45) Date of Patent: Feb. 19, 2008

(54) SYSTEM AND METHOD FOR MULTIPLE ELECTRON, ION, AND PHOTON BEAM ALIGNMENT

(75) Inventors: Lawrence Muray, Moraga, CA (US); James Spallas, Alamo, CA (US)

(73) Assignee: Novelx, Inc., Lafayette, GA (US)

( * ) Notice: Subject to any disclaimer, the term of this patent is extended or adjusted under 35 U.S.C. 154(b) by 354 days.

(21) Appl. No.: 11/160,227

(22) Filed: Jun. 14, 2005

Related U.S. Application Data

(60) Provisional application No. 60/580,953, filed on Jun. 18, 2004.

(51) Int. Cl.
 *G01N 23/00* (2006.01)
(52) U.S. Cl. ................... 250/491.1; 378/20
(58) Field of Classification Search .......... 250/491.1, 250/492.2, 492.21, 396; 378/20
 See application file for complete search history.

(56) References Cited

U.S. PATENT DOCUMENTS

| | | | | |
|---|---|---|---|---|
| 3,876,883 A | * | 4/1975 | Broers et al. | 250/492.1 |
| 4,724,324 A | * | 2/1988 | Liebert | 250/397 |
| 4,917,490 A | * | 4/1990 | Schaffer et al. | 356/152.1 |
| 4,967,088 A | * | 10/1990 | Stengl et al. | 250/491.1 |
| 5,122,663 A | | 6/1992 | Chang et al. | |
| 5,155,412 A | | 10/1992 | Chang et al. | |
| 5,506,681 A | * | 4/1996 | Igaki | 356/616 |
| 5,905,266 A | * | 5/1999 | Larduinat et al. | 250/492.21 |
| 6,137,111 A | * | 10/2000 | Yamada et al. | 250/492.2 |
| 6,140,654 A | * | 10/2000 | Nakasugi et al. | 250/491.1 |
| 6,222,195 B1 | * | 4/2001 | Yamada et al. | 250/492.2 |
| 6,288,401 B1 | | 9/2001 | Chang et al. | |
| 6,617,587 B2 | * | 9/2003 | Parker et al. | 250/398 |
| 6,765,673 B1 | * | 7/2004 | Higashikawa | 356/399 |
| 6,870,171 B2 | * | 3/2005 | Hosoda et al. | 250/492.22 |
| 2003/0085360 A1 | * | 5/2003 | Parker et al. | 250/396 R |
| 2003/0211409 A1 | * | 11/2003 | Nunes | 430/22 |

FOREIGN PATENT DOCUMENTS

JP 10187979 A * 7/1998

OTHER PUBLICATIONS

B. Boegli et al., Automatic Mark Detection in Electron Beam Nanolithography Using Digital Image Processing and Correlation. *J. Vac. Sci. Technol.* B8(6) Nov./Dec. 1990 pp. 1994-2001.
T.H.P. Chang et al., "Multiple Electron-Beam Lithography," *Microelectronic Engineering*, 2001, pp. 1-26.
L.P. Muray et al., "Advances in Arrayed Microcolumn Lithography," *J. Vac. Sci. Technol. B*, Nov./Dec. 2000, pp. 3099-3104, vol. 18, No. 6, American Vacuum Society, New York, U.S.A.

* cited by examiner

*Primary Examiner*—Nikita Wells
*Assistant Examiner*—Michael Maskell
(74) *Attorney, Agent, or Firm*—Thelen Reid Brown Raysman & Steiner; Aaron Wininger

(57) ABSTRACT

A beam column array included alignment marks within to enable alignment of beams with respect to each other. Specifically, the array includes an array of beam columns, each column having at least once lens. A plurality of alignment marks are located beneath the lens. A method of using the array includes: scanning a plurality of beams in a beam column array over a plurality of alignment marks; and determining beam centroid positions of the beams with respect to each other based on data from the scanning.

28 Claims, 6 Drawing Sheets

To Column
Array

SYSTEM AND METHOD FOR MULTIPLE ELECTRON, ION, AND PHOTON BEAM ALIGNMENT

PRIORITY REFERENCE TO PRIOR APPLICATION

This application claims benefit of and incorporates by reference U.S. patent application Ser. No. 60/580,953, entitled "In-Situ Multiple Beam Registration Techniques Using Integrated Patterned Apertures," filed on Jun. 18, 2004, by inventors Lawrence P. Muray, et al.

TECHNICAL FIELD

This invention relates generally to electron, photon, and ion beam (collectively referred to as beams) columns, and more particularly, but not exclusively, provides a system and method for multiple beam alignment in a plurality of beam columns using alignment marks on the columns.

BACKGROUND

Electron beam columns are used in scanning electron microscopes (SEMs) that image objects and in lithography tools for writing patterns onto semiconductor materials to be used as integrated circuits. Conventional electron beam columns consist of an assembly of components, including lenses, magnets, deflectors, blankers, etc., individually machined out of stainless steel or other alloys and individually assembled, and an electron source.

Alternatively, miniature electron beam columns can be made by using, in part, micro-fabricated lenses, deflectors and blankers. These components are fabricated in silicon using micro-electromechanical systems (MEMS) fabrication technologies. Each component consists of vertically stacked silicon lenses that are electrically isolated by dielectric spacers, like, for example, glass. The silicon and glass elements have at least one aperture concentric with very other aperture creating a path for the electron beam to transverse. The components are energized to focus, blank, and steer the electron beam.

Focused electron, ion or photon beams are a proven technique of achieving extremely high-resolution, high-placement accuracy imaging, patterning and analysis. A major limitation of these techniques, however, is the serial manner in which each pixel on a work surface must be addressed, whether for writing or for imaging, which can result in unacceptably low throughputs. A well-known technique for increasing throughput linearly or quadraticly is to use linear or rectangular arrays of beams which operate in parallel. In this way, the resolution of the beam may be fully utilized without suffering unacceptable losses in wafer or sample throughput.

To this end, a number of parallel, distributed beam techniques have been introduced including miniature microfabricated beam columns (microcolumns), zone plate arrays (ZPAL), distributed variable/fixed aperture electron beam systems (DIVA/DIFA), and massively parallel beam systems (MAPPER). A common shortcoming of these systems however is the inability to accurately register (align) one beam to another and thereby meet the placement accuracy required in future generation lithography and inspection tools. Although a number of techniques have been proposed to address this issue, mostly based on marks on a wafer or substrate, these techniques are generally either too impractical, too time-consuming or too inaccurate for implementation in a production tool.

Miniature microfabricated beam columns are particularly amenable to parallel operation in linear or rectangular array by the nature of the MEMS processes used in fabrication and the small footprint of the column. The columns may be individually assembled or monolithically fabricated into linear or rectangular arrays and operated in parallel. The actual size and shape of the arrays are primarily dictated by the writing or reading strategy adopted at the system level. A major problem however, as discussed above for all distributed axis beam systems, is beam-to-beam calibration. Even with nanometer level placement of the lens apertures, variations in assembly tolerances, accuracy of tip placement, tip temperature, source alignment, etc., an extremely reliable and efficient system and method of beam to beam alignment is required.

SUMMARY

An apparatus and method are provided that enable the calibration of multiple beams in a beam array to each other. In an embodiment of the invention, the apparatus comprises an array of beam columns, each column having at least one lens; and a plurality of alignment marks located beneath the lens. The apparatus can further comprise electronics coupled to the array that are capable of receiving data after the beams scan the marks and then determine beam centroid positions with respect to each other based on the received data. Further, a beam can be scanned over a mark on a target so that the electronics can determine the position of the beam relative to the target. Once the beam centroid positions are known, the beams can be aligned with respect to each other and the target.

In an embodiment of the invention, the method comprises scanning a plurality of beams in a beam column array over a plurality of alignment marks, each column having at least one lens with the marks located beneath; scanning a mark on a target with a beam from the plurality and determining beam centroid positions of the beams with respect to each other and the target based on data from the scanning. Once the beam centroid positions are known, the beams can be aligned with respect to each other and the target.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION OF THE
ILLUSTRATED EMBODIMENTS

The following description is provided to enable any person having ordinary skill in the art to make and use the invention, and is provided in the context of a particular application and its requirements. Various modifications to the embodiments will be readily apparent to those skilled in the art, and the principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
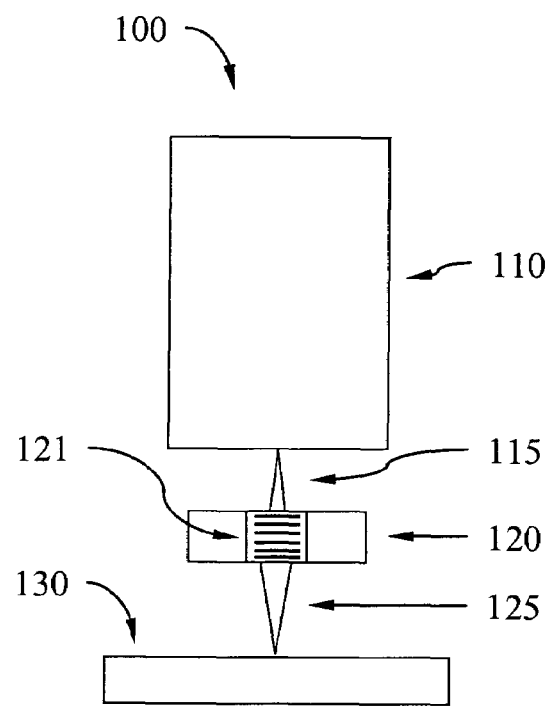
FIG. 1 is a block diagram illustrating an apparatus incorporating an electron beam column having alignment marks.

FIG. 1 is a block diagram illustrating an apparatus 100 incorporating a beam column package 120. In embodiments of the invention, the apparatus 100 includes scanning electron microscopes, lithography, inspection, and analysis tools. The apparatus 100 includes a source 110 (e.g., cathode), such as an thermal field emitter (TFE) for emitting electrons, positioned adjacent to a beam column package 120, which supports the lenses, deflectors, blankers, magnetic or electrostatic, and/or other elements required for the column operation (heretofore components) 121. The package 120 and components 121 form the package assembly which is positioned adjacent to a sample holder 130. In an embodiment of the invention, the source 110 is positioned above the beam column package 120 and the sample holder 130 is positioned below the beam column package 120.

In an embodiment of the invention, the source 110 emits electrons 115 by field assisted thermionic emission. The source 110 can also comprise a Tungsten or $LaB_6$ filament, or any of a multitude of cold field emitters, including carbon nanotubes and microfabricated field emission tips. The electrons 115 can have an energy ranging from a few hundred eV to up to about 5 keV. The components 121 coupled to the beam column package 120, which will be discussed in further detail below, extract, collimate, and focus the electrons 115 into an electron beam 125, which is emitted from the package assembly as an electron beam 125. The package assembly scans the focused beam 125 over the sample holder 130.

In an embodiment in which the apparatus 100 includes a scanning electron microscope, the sample holder 130 holds an object for viewing. The beam 125 strikes the object causing the emission of electrons which are detected by a detector (not shown), such as a micro-channel plate (MCP), mounted, in one embodiment, to a mounting plate (not shown) attached to the bottom of the beam column package 120. In an embodiment of the invention, an Everhart-Thornley detector can be used in addition to or in place of the MCP device in order to detect back-scattered and secondary electrons. The detected electrons are then used to generate an image of the object. In an embodiment of the invention, a silicon drift detector (SDD) or other photon detector can be used in addition to or in place of the MCP device in order to detect photons. The detected photons are then used for materials identification and analysis.

In an embodiment in which the apparatus 100 includes a lithography tool, the sample holder 130 holds a substrate onto which patterns for integrated circuits are written by the apparatus 100. The apparatus 100 includes a blanker to blank emission of electrons when necessary to generate the correct pattern on the substrate.

Figure 2:
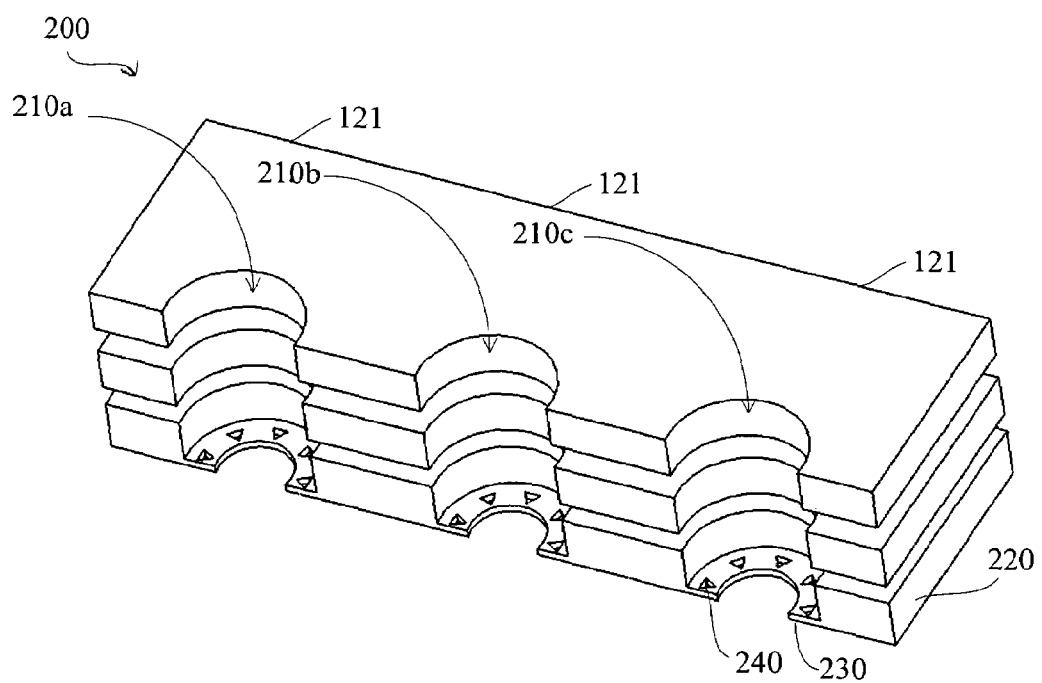
FIG. 2 is a cross section of an array of final objective lenses incorporating alignment marks.

FIG. 2 is a cross section of an array of final objective lenses 200 incorporating alignment (registration) marks. The objective lenses 200 are each part of a beam column package 120. The objective lenses 200 include an array of three components 121, e.g., objective lenses 210a, 210b and 210c, arranged in a line as part of beam columns (not shown). In other embodiments of the invention, there can be additional or fewer beam columns and the beam columns can be arrayed in different patterns.

In an embodiment of the invention, a silicon microfabricated aperture array 230 with one or more precisely patterned alignment features (also referred to as marks) 240 (through-wafer features or, alternatively for in-lens systems, other surface features) placed just below the lenses 200, or other suitable location, on or in a multibeam system such as a SEM array. In an embodiment of the invention, the arrays 230 can be patterned into a bottom layer 220 of the lenses 200. Beam detectors can be located beneath the marks 240.

Under normal operation, the aperture array 230 is grounded (or biased appropriately) and thus allows the beam 125 to pass unobstructed, with no undesirable effect on the beam resolution. During calibration, however, parallel beams are deflected beyond the normal deflection field and strike the precisely patterned alignment features 240. Conventional mark detection routines, or other routines described below, can then be used to individually align each beam 125 to the marks at the nanometer level. Since the alignment marks are placed lithographically, and are thus also aligned to the nanometer level, the beam-to-beam alignment will also approach this level. Since the aperture/mark component (AMC) is a part of the beam delivery system, this calibration can be performed at any time during column operation, including initially, after each scan or at timed intervals. Alignment of the columns can take place simultaneously (with appropriate electronics) and thereby avoid the time-consuming serial alignment of individual columns with a mark patterned on the sample, for example.

In the embodiment of FIG. 2, the aperture/mark component is an integral part of the final lens of the SEM. The aperture is fabricated from a single silicon substrate or from a silicon-on-insulator (SOI) wafer 220 which comprises the final lens element of the SEM as well as the AMC. The simplicity of the latter embodiment of the invention makes it particularly favorable for production. The marks are through-wafer patterns which enable easy detection of secondary or backscatter electrons with the standard SEM detectors.

The shape and number of marks 240 may be significant and depends on the specific algorithm chosen for alignment. In the embodiment of FIG. 2, triangular shapes are illustrated, which may be appropriate for "dynamic" alignment techniques described below, but other shapes or patterns, e.g., Barker codes or crosses, can easily be accommodated. In an embodiment, the marks 240 are active, electron or photon sensing devices (e.g., PN junctions) and thereby eliminate the requirement for an external detector. The important features of the AMC in this embodiment is that all patterns on the critical layer, including the aperture, are precisely placed using high-resolution lithography techniques (e.g., direct write e-beam) and the substrate (silicon in this case) is thermally matched to the column array.

Since the plane of the aperture/marks is different from the plane of imaging/writing, some care must be taken in determining the exact location (i.e., centroid) of the beam on the writing/imaging surface. If the beam is refocused onto the AMC, a calibration must exist apriori which can map AMC locations to the substrate (or other object, generically referred to as target) locations. If the beam is not refocused, a methodology must be used that can precisely place the position of an enlarged (out-of-focus) beam.

Another consideration for the AMC is the radial position of the alignment marks 240. If the marks 240 are far from field center, higher order deflection aberrations become important which can unnecessarily complicate the alignment calibration. At the other extreme, alignment marks that extend into the standard deflection field cause no additional field related aberrations, but reduce the available patterning/imaging area. A suitable tradeoff between the two extremes can be determined on a case by case basis.

Figure 3A:
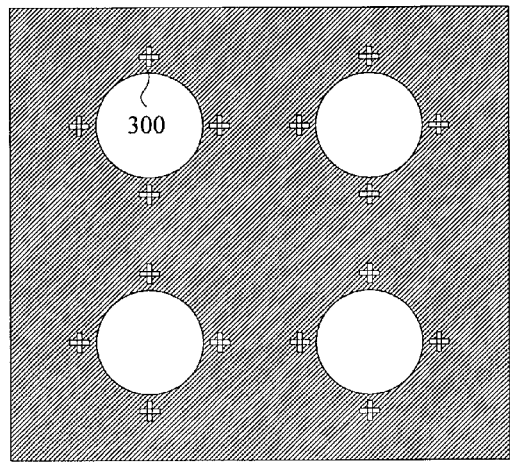
FIGS. 3A and 3B are diagrams illustrating alignment marks according to another embodiment of the invention.
Figure 3B:
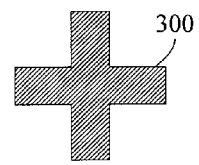
Figure 4A:
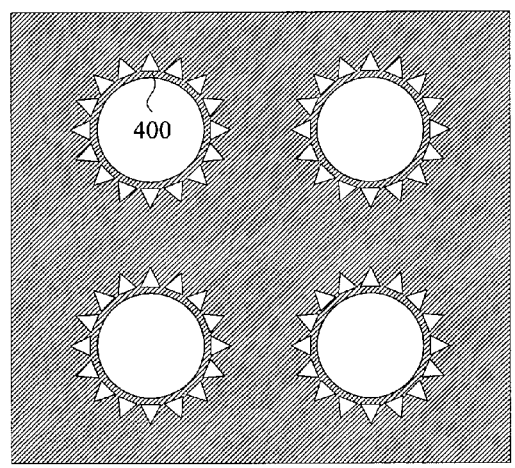
FIGS. 4A and 4B are diagrams illustrating alignment marks according to another embodiment of the invention.
Figure 4B:
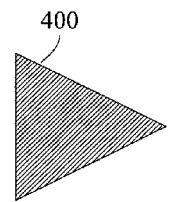
Figure 5A:
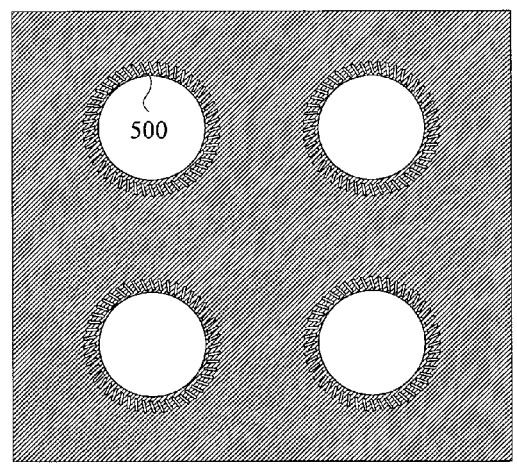
FIGS. 5A and 5B are diagrams illustrating alignment marks according to another embodiment of the invention.
Figure 5B:
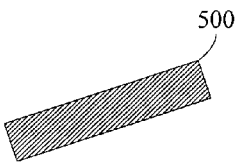

FIG. 3A-FIG. 5B are diagrams illustrating additional embodiments of marks. In FIG. 3A and FIG. 3B, the array includes marks 300 having a cross shape. In FIG. 4A and FIG. 4B, the array includes marks 400 having a triangular shape pointing outwards from the column. In FIG. 5A and FIG. 5B, the array includes marks 500 having a rectangular shape with a slanted offset from the column. The marks 300, 400 and 500 are generally about 1-10 microns in each dimension and each array includes at least 3 marks, 300, 400 or 500 and preferably at least 4 marks. Further, the more marks per array will increase calibration accuracy.

Figure 6:
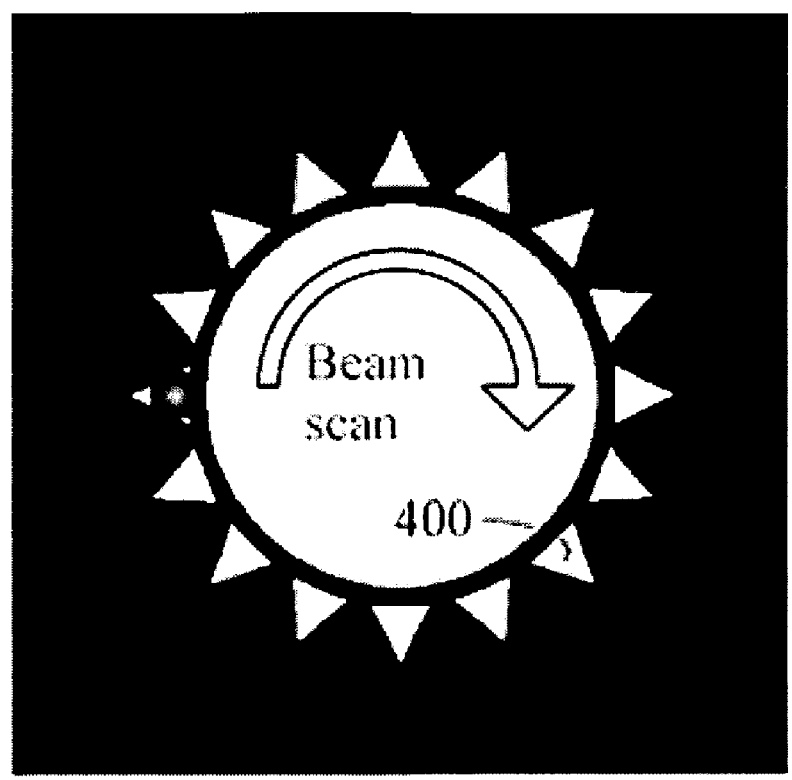
FIG. 6 is a diagram illustrating a circular scanning of a beam along alignment marks.
Figure 7:
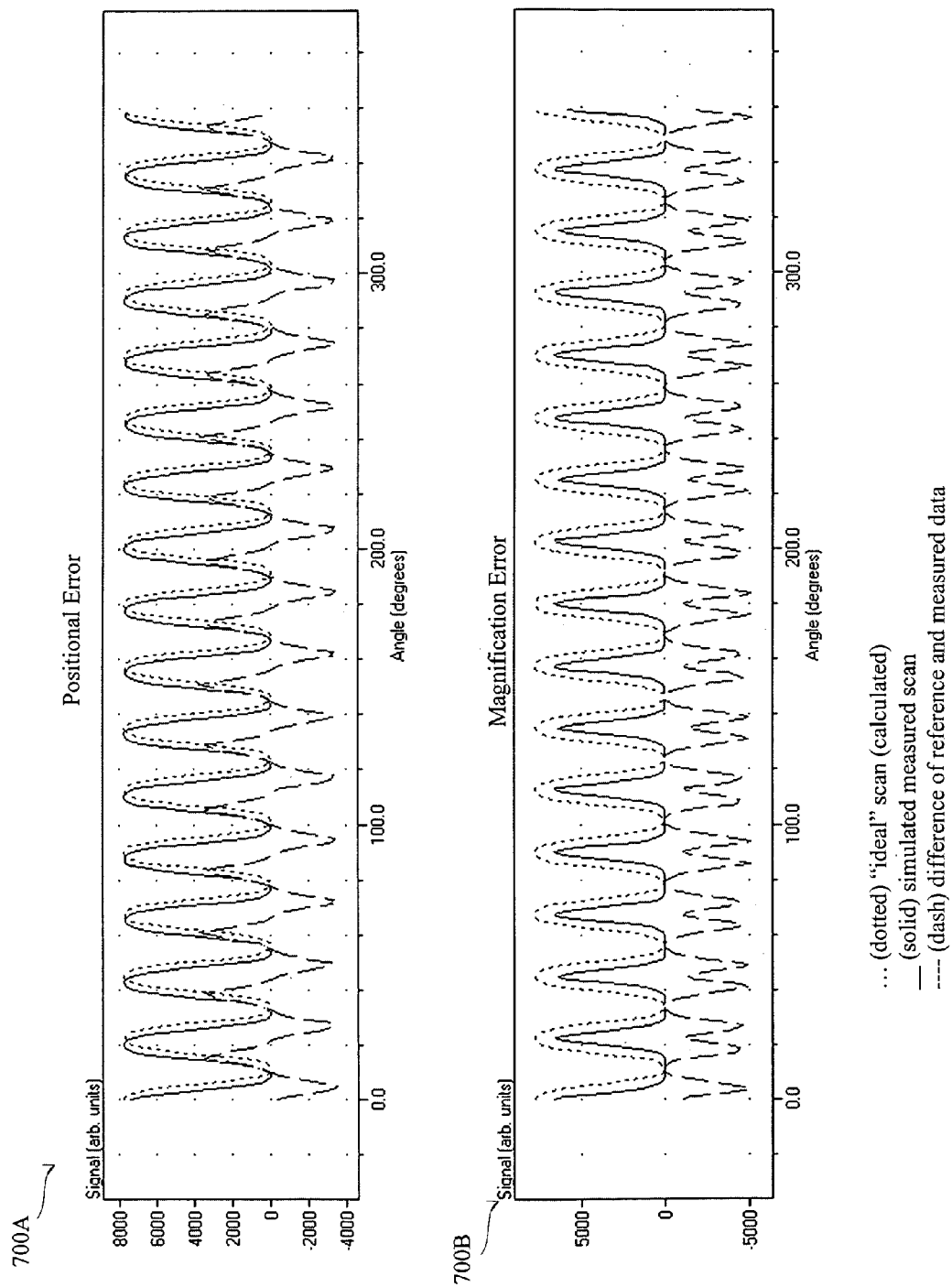
FIG. 7 are charts illustrating simulated results of the beam scanning of FIG. 6 showing deflection errors.

FIG. 6 is a diagram illustrating a circular scanning of a beam along alignment marks to locate beams relative to each other according to a dynamic mode mark detection technique and FIG. 7 includes charts illustrating simulated results of the beam scanning of FIG. 6 showing deflection errors. In a dynamic mode, the marks are distributed radially around the AMC aperture at 8 or more locations. The marks can taper inward, outward, or consist of simple lines (as show in FIG. 3A-FIG. 4D). Embodiments of the invention rely on scanning the beams (in parallel) in a fixed radius over the marks and comparing the resulting linescans between columns as well as to "ideal" linescans. The periodicity, the pulsewidth and the phase of the linescan per full rotation directly relate to the errors in the centroid and scaling of the fields. By comparison with an "ideal" scan or from column-to-column, the beam-to-beam scan errors can be minimized. A sample of an AMC and the simulated resultant linescans for the case of a beam positional error (upper graph 700A) and magnification error (lower graph 700B) is shown in FIG. 7. The dotted lines represent the "ideal" signal expected from a perfectly calibrated deflection system, the solid lines are the simulated signals including calibration errors and the dashed lines are the difference between the two. In this case the beam is assumed to be a defocused Gaussian beam.

Several metrics can be used to determine the accuracy of the alignment, including a simple subtraction from the "ideal" signal and integration of the difference signals or a measure of phase error from one signal to the other with a lock-in amplifier. If the system includes high speed blankers, such as miniature column arrays, stroboscopic techniques may also be used to evaluate alignment errors. For example, one alignment method is real-time generation of Moire patterns which can greatly amplify extremely small errors.

This technique alone is most likely not sufficient to fully calibrate a new system, but it is well suited for small changes to an existing calibration, or as a check of the state of column to column calibration. It is conceivable that the latter may be performed as frequently as at the end of every frame or other suitable testing point. Again, since all the beams are scanned in a circle in parallel the overhead time associated with these scans is independent of the array size.

For more accurate alignment, a static mode mark detection technique can be used. In static mode, the beams are deflected in parallel to the first alignment marks, the marks are scanned, and then the mark position is determined by conventional location techniques. The procedure is repeated for each mark. Some well known methods of determining position are correlations, center-of-mass methods and edge detection schemes. Generally, methods using image processing instead of line scans produce more accurate results at the cost of increased scan and process time. The number of marks scanned and the location of scanned marks is algorithm dependent but generally consists of at least four marks located along the +X, -X, +Y and -Y axis. The more marks scanned, the better averaging occurs and the more accurately the position can be determined.

This method can produce the best positional accuracy and is well suited for full system calibration or periodic recalibration. The technique allows column-to-column calibration of the entire array and then a single column to substrate alignment procedure. As such, the substrate need have only one mark for alignment instead of multiple marks for alignment of each column or if the substrate has one mark, there is no need move the columns or substrates with respect to each other to scan the substrate mark, thereby increasing speed of alignment. Accordingly, irrespective of array size, only two calibrations are required to calibrate the entire array.

Figure 8:
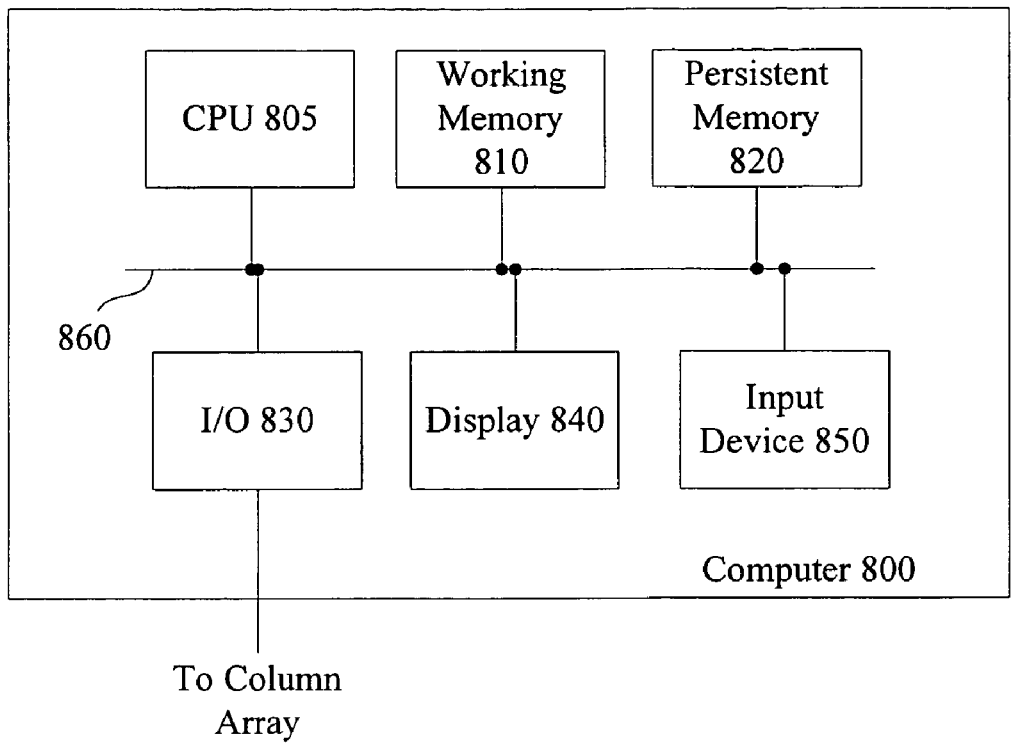
FIG. 8 is a block diagram illustrating a computer communicatively coupled to a beam column array capable of determining beam locations.

FIG. 8 is a block diagram illustrating a computer 800 communicatively coupled to a beam column array capable of determining beam locations. The computer 800 includes a central processing unit (CPU) 805; working memory 810; persistent memory 820; input/output (I/O) interface 830; display 840; and input device 850, all communicatively coupled to each other via a bus 860. The CPU 805 may include an INTEL PENTIUM microprocessor, a Motorola POWERPC microprocessor, or any other processor capable to execute software stored in the persistent memory 820. The working memory 810 may include random access memory (RAM) or any other type of read/write memory devices or combination of memory devices. The persistent memory 820 may include a hard drive, read only memory (ROM) or any other type of memory device or combination of memory devices that can retain data after the computer 800 is shut off. The I/O interface 830 is communicatively coupled, via wired or wireless techniques, to an array of scanning electron microscope having alignment marks. The display 840 may include a flat panel display, cathode ray tube display, or any other display device. The input device 850, which is optional like other components of the invention, may include a keyboard, mouse, or other device for inputting data, or a combination of devices for inputting data.

One skilled in the art will recognize that the computer 800 may also include additional devices, such as network connections, additional memory, additional processors, LANs, input/output lines for transferring information across a hardware channel, the Internet or an intranet, etc. One skilled in the art will also recognize that the programs and data may be received by and stored in the system in alternative ways. Further, in an embodiment of the invention, an Application Specific Integrated Circuit (ASIC) is used in place of the computer 800.

Figure 9:
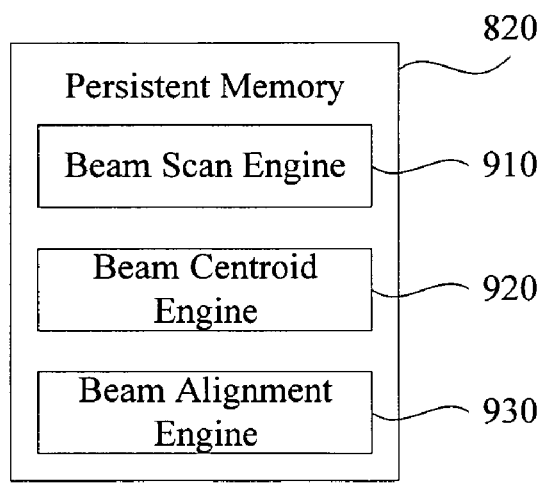
FIG. 9 is a block diagram illustrating a memory of the computer of FIG. 8.

FIG. 9 is a block diagram illustrating the persistent memory 820 of the computer 800. The persistent memory 820 includes a beam scan engine 910, a beam centroid engine 920, and a beam alignment engine 930. The beam scan engine 910 causes deflectors or other components 121 to scan the beams over marks 240 in the aperture array 230 and to scan a single column beam over a mark on a substrate. The beam centroid engine 920 receives data from detectors beneath the aperture array 230 or from the marks themselves if they are active and then determines the centroid of the beams using a dynamic and/or static mode technique as discussed above. The beam alignment engine 930 receives data from the mark on the substrate (if active) or from a detective positioned beneath the substrate mark and then determines the alignment of the beams with respect to the substrate.

Figure 10:
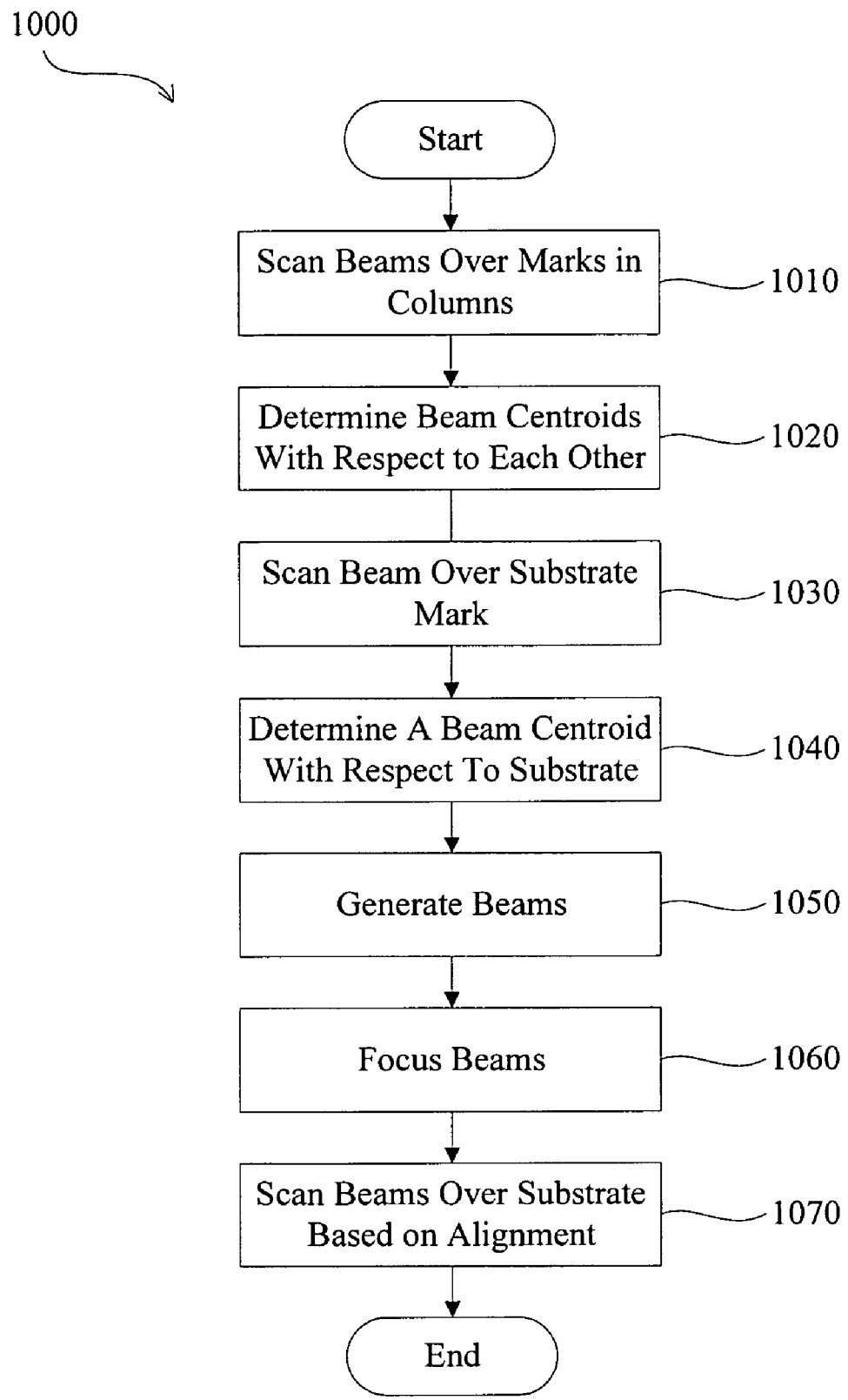
FIG. 10 is a flowchart illustrating a method aligning beams and imaging a sample using the aligned beams.

FIG. 10 is a flowchart illustrating a method aligning beams and imaging a sample using the aligned beams. First, beams are scanned (1010) over marks in the columns. Then based on collected data from the scanning (1010), the centroids of the beams are determined (1020) relative to each other. A single beam is then scanned (1030) over a mark in a substrate. Based on data from the scanning (1030), a beam centroid is determined (1040) relative to the substrate and therefore, all centroid positions are then known relative to the substrate. Beams are then generated (1050) and focused (1060). The beams are then scanned (1070) over a substrate based on the locations of the centroids relative to each other and the substrate. The method 1000 then ends.

The foregoing description of the illustrated embodiments of the present invention is by way of example only, and other variations and modifications of the above-described embodiments and methods are possible in light of the foregoing teaching. For example, while the above embodiments describe using the packages for electrons, charged particles (ions) of any type or photons could be used in place of or in addition to electrons. Further, the column array can be used in many applications besides imprinting patterns onto substrates. In addition, connections may be wired, wireless, modem, etc. The embodiments described herein are not intended to be exhaustive or limiting. The present invention is limited only by the following claims.

What is claimed is:

1. An apparatus, comprising:
    an array of beam columns, each column having at least one lens;
    a plurality of alignment marks located beneath the lens; and
    electronics coupled to the array capable of receiving data after beams scan the marks and to determine beam centroid positions with respect to each other based on the received data using a static or dynamic mode technique.

2. The apparatus of claim 1, wherein the alignment marks are patterned into a bottom layer of the lenses.

3. The apparatus of claim 1, wherein the alignment marks are active.

4. The apparatus of claim 1, further comprising detectors located beneath the marks.

5. The apparatus of claim 1, wherein the electronics determine beam centroid positions with respect to each other using a static mode technique.

6. The apparatus of claim 1, wherein the electronics determine beam centroid positions with respect to each other using a dynamic mode technique.

7. The apparatus of claim 1, wherein the electronics are further capable of determining a beam centroid position with respect to a mark on a target.

8. The apparatus of claim 1, wherein there are at least 4 marks per column.

9. A method, comprising:
    scanning a plurality of beams in a beam column array over a plurality of active alignment marks, each column having at least one lens with the marks located beneath; and
    determining beam centroid positions of the beams with respect to each other based on data from the scanning.

10. The method of claim 9, wherein the alignment marks are patterned into a bottom layer of the lenses.

11. The method of claim 9, further comprising detectors located beneath the marks.

12. The method of claim 9, wherein the determining determines beam centroid positions with respect to each other using a static mode technique.

13. The method of claim 9, wherein the determining determines beam centroid positions with respect to each other using a dynamic mode technique.

14. The method of claim 9, further comprising determining a beam centroid position with respect to a mark on a target.

15. The method of claim 9, wherein there are at least 4 marks per column.

16. A system, comprising:
    means for scanning a plurality of beams in a beam column array over a plurality of alignment marks, each column having at least one lens with the marks located beneath; and
    means for determining beam centroid positions of the beams with respect to each other based on data from the scanning using a dynamic mode or static mode technique.

17. A computer readable medium having stored thereon instructions to cause a computer to execute a method, the method comprising:
    causing a scanning a plurality of beams in a beam column array over a plurality of alignment marks, each column having at least one lens with the marks located there beneath; and
    determining beam centroid positions of the beams with respect to each other based on data from the scanning using a dynamic mode or static mode technique.

18. A system, comprising:
    a beam scan engine capable of causing a scanning of a plurality of beams in a beam column array over a plurality of alignment marks, each column having at least one lens with the marks located there beneath; and
    a beam centroid engine capable of receiving data based on the scanning and determining beam centroid positions relative to each other based on the data using a static or dynamic mode technique.

19. The system of claim 18, wherein the beam scan engine is further capable of causing a scanning of a beam from the array over a mark on a target, and wherein the system further comprises a beam alignment engine capable of determining a position of a beam centroid from the plurality of beams with respect to a mark on a target based on the scanning of the target mark.

20. A method, comprising:
    scanning a plurality of beams in a beam column array over a plurality of alignment marks, each column having at least one lens with the marks located beneath; and
    determining beam centroid positions of the beams with respect to each other based on data from the scanning using a dynamic mode or static mode technique.

21. The method of claim 20, wherein the alignment marks are patterned into a bottom layer of the lenses.

22. The method of claim 20, wherein the alignment marks are active.

23. The method of claim 20, further comprising detectors located beneath the marks.

24. The method of claim 20, further comprising determining a beam centroid position with respect to a mark on a target.

25. The method of claim 20, wherein there are at least 4 marks per column.

26. A system, comprising:
  means for scanning a plurality of beams in a beam column array over a plurality of active alignment marks, each column having at least one lens with the marks located beneath; and
  means for determining beam centroid positions of the beams with respect to each other based on data from the scanning.

27. A computer readable medium having stored thereon instructions to cause a computer to execute a method, the method comprising:
  causing a scanning a plurality of beams in a beam column array over a plurality of active alignment marks, each column having at least one lens with the marks located there beneath; and
  determining beam centroid positions of the beams with respect to each other based on data from the scanning.

28. A system, comprising:
  a beam scan engine capable of causing a scanning of a plurality of beams in a beam column array over a plurality of active alignment marks, each column having at least one lens with the marks located there beneath; and
  a beam centroid engine capable of receiving data based on the scanning and determining beam centroid positions relative to each other based on the data.

* * * * *

UNITED STATES PATENT AND TRADEMARK OFFICE
CERTIFICATE OF CORRECTION

PATENT NO. : 7,332,729 B1 Page 1 of 1
APPLICATION NO. : 11/160227
DATED : February 19, 2008
INVENTOR(S) : Lawrence P. Muray et al.

It is certified that error appears in the above-identified patent and that said Letters Patent is hereby corrected as shown below:

Title Page, Item (73) Assignee:
Delete "GA" and Insert -- CA --.

Signed and Sealed this

Twenty-sixth Day of August, 2008

JON W. DUDAS
*Director of the United States Patent and Trademark Office*